United States Patent [19]

Metcalf et al.

[11] 4,118,424
[45] Oct. 3, 1978

[54] BIODEGRADABLE INSECTICIDES

[75] Inventors: Robert L. Metcalf; Joel R. Coats, both of Urbana, Ill.

[73] Assignee: University of Illinois Foundation, Urbana, Ill.

[21] Appl. No.: 694,458

[22] Filed: Jun. 9, 1976

Related U.S. Application Data

[62] Division of Ser. No. 520,370, Nov. 4, 1974, Pat. No. 4,003,950.

[51] Int. Cl.$^2$ ............................................. C07C 43/20
[52] U.S. Cl. ................................................. 260/613 R
[58] Field of Search ..................................... 260/613 R

[56] References Cited

U.S. PATENT DOCUMENTS 2,883,428  4/1959  Nemec et al. ..................... 260/613 R

FOREIGN PATENT DOCUMENTS 1,936,494  1/1970  Fed. Rep. of Germany ...... 260/613 R

OTHER PUBLICATIONS

Rogers et al., J.A.C.S., vol. 75 (1953), 2991-2994.

*Primary Examiner*—Bernard Helfin
*Attorney, Agent, or Firm*—Merriam, Marshall & Bicknell

[57] ABSTRACT

Biodegradable insecticides having the formula:

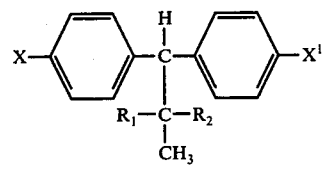

where $R_1$ is H or Cl, $R_2$ is $CH_3$ or Cl, X and $X^1$ are the same or different and each is selected from the group consisting of $C_1$ to $C_3$ alkyl groups and $C_1$ to $C_4$ alkoxy groups.

2 Claims, No Drawings

BIODEGRADABLE INSECTICIDES

This is a division of application Ser. No. 520,370, filed Nov. 4, 1974 and now U.S. Pat. No. 4,003,950.

SUMMARY OF THE INVENTION

The present invention relates to improved insecticides. In general, it concerns highly insecticidal, yet biodegradable compositions which exhibit low toxicity to mammals. More particularly, it pertains to new compounds which are metabolically biodegradable in living organisms yet are persistnet insecticides having the formula:

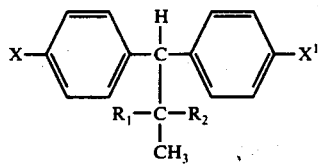

where $R_1$ is H or Cl, $R_2$ is $CH_3$ or Cl, X and $X^1$ are the same or different and each is selected from the group consisting of $C_1$ to $C_3$ alkyl groups and $C_1$ to $C_4$ alkoxy groups.

BACKGROUND OF THE INVENTION

In U.S. Pat. No. 3,787,505, Metcalf et al. disclosed certain asymmetrical DDT analogues, as well as methods for providing and selectively controlling the biodegradability of certain DDT analogues. The DDT analogue molecules disclosed in U.S. Pat. No. 3,737,505 all have an aliphatic —$CCl_3$ moiety or portion which is, of course, also present in DDT (1,1,1 -trichloro-2,2-bis(p-chlorophenyl) ethane.

The asymmetrical biodegradable insecticides disclosed in U.S. Pat. No. 3,787,505 have provided a means for solving the environmental pollution problems which are associated with the use of DDT. In addition, as a result of the discoveries disclosed in U.S. Pat. No. 3,787,505, we have made efforts to discover additional DDT-like compounds which would exhibit improved biodegradability, be persistent, and highly insecticidal.

DESCRIPTION OF THE INVENTION

We have studied the replacement of the aliphatic —$CCl_3$ portion of certain DDT derivatives and have discovered that some other aliphatic groups produce new compounds which are not only insecticidal and persistent, but also exhibit improved biodegradability.

The aliphatic groups which we have found particularly useful are those which can be represented by the formula: —$C(CH_3) R_1R_2$, where $R_1$ is H or Cl and $R_2$ is $CH_3$ or Cl.

Metabolic studies involving insects, mice, and fish and a model ecosystem (such as described in U.S. Pat. No. 3,787,505) and insecticidal activity studies generally involving flies and mosquitoes have shown that both the symmetrical and the asymmetrical compounds of the present invention are effective. Thus, the new compounds can be represented by the general formula:

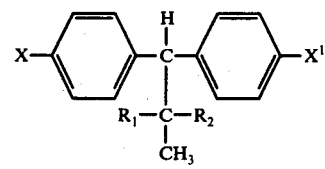

where $R_1$ is H or Cl and $R_2$ is $CH_3$ or Cl, X and $X^1$ are the same or different and each is selected from the group consisting of $C_1$ to $C_3$ alkyl groups and $C_1$ to $C_4$ alkoxy groups.

The preparation or synthesis of the compounds of the present invention can be accomplished by so-called Baeyer condensation or Friedel-Crafts reactions between appropriate substituted benzene(s) e.g., toluene or anisole, and an appropriate aliphatic aldehyde, e.g., 2-chloropropionaldehyde, etc., as more fully described hereafter.

The present invention can be further illustrated by reference to the following examples. Example I illustrates the preparation of dianisyl-2-chloropropane.

EXAMPLE I

Dianisyl-2-chloropropane (i.e., 1,1-bis(p-methoxy phenyl)-2-chloropropane) is synthesized as follows: Two moles of anisole and one mole of 2-chloropropionaledehyde are added dropwise into about 5 volumes of a cold concentrated acid mixture consisting of a 1:1 mixture of glacial acetic acid and concentrated sulfuric acid, maintained at about 0° C. by use of an ice bath. The reaction product is recovered after crystallization from ethanol, yielding white needle-shaped particles having a melting point of about 78° C. The structure can be confirmed by nmr: The γ-carbon protons absorb as a doublet at δ1.35 and δ1.45, the methoxy protons as two singlets at δ3.617 and δ3.633, the α-proton as a doublet at δ3.790 and δ3.950, and β-proton as a multiplet at δ4.330 – δ4.818.

Dianisyl-2-chloropropane ("DCP") was tested for insecticidal activities using standard methods and compared with the activities of DDT and methoxychlor. In addition, DCP was tested for mouse toxicity, fish toxicity and biodegradibility. The results of such tests are set forth in Table I.

TABLE I

| Compound | Housefly Activities Topical LD$_{50}$, μg./g. | | | | Mouse Toxicity Oral LD$_{50}$, μg./g. | Fish (Gambusia) Toxicity LC$_{50}$, ppm | Biodegradability | | | |
|---|---|---|---|---|---|---|---|---|---|---|
| | S$_{NAIDM}$[a] | | R$_{SP}$[c] | | | | B.I.[d] | | E.M.[e] | |
| | alone | with P.B.[b] | alone | with P.B. | | | fish | snail | fish | snail |
| DDT | 14.0 | 5.5 | 270 | 70 | 200 | 0.30 | 0.015 | 0.045 | 84,500 | 34,500 |
| Methoxychlor | 45.0 | 3.5 | 48 | 4.6 | 1000 | 1 | 0.94 | 0.13 | 1,545 | 120,000 |

TABLE I-continued

| | Housefly Activities Topical LD$_{50}$, µg./g. | | | | Mouse Toxicity Oral LD$_{50}$, µg./g. | Fish (Gambusia) Toxicity LC$_{50}$, ppm | Biodegradability | | | |
|---|---|---|---|---|---|---|---|---|---|---|
| | S$_{NAIDM}$[a] | | R$_{SP}$[c] | | | | B.I.[d] | | E.M.[e] | |
| Compound | alone | with P.B.[b] | alone | with P.B. | | | fish | snail | fish | snail |
| DCP (Example 1) | 935 | 3.5 | >500 | 4.1 | >1000 | >3 | 1.35 | 0.18 | 1,340 | 66,430 |

[a] } = susceptible strain
[b] = piperonyl butoxide synergist
[c] = resistant strain
[d] = B.I. = biodegradability index = $\frac{\text{concentration of polar metabolites}}{\text{concentration of non-polar metabolities}}$
[e] = E.M. = environmental magnification = $\frac{\text{concentration of parent compound in organism}}{\text{concentration of parent compound in water}}$

TABLE II

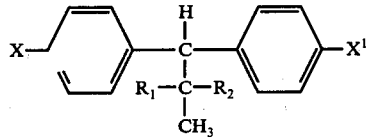

| Example No. | R$_1$ | R$_2$ | X | X$^1$ | M.P.° C. |
|---|---|---|---|---|---|
| I | H | Cl | OCH$_3$ | OCH$_3$ | 78 |
| II | H | Cl | CH$_3$ | CH$_3$ | liquid |
| III | H | Cl | CH$_3$ | OC$_2$H$_5$ | liquid |
| IV | H | Cl | OCH$_3$ | OC$_2$H$_5$ | 38 |
| V | H | Cl | OC$_2$H$_5$ | OC$_2$H$_5$ | 47–8 |
| VI | H | Cl | OC$_2$H$_5$ | OC$_3$H$_7$ | liquid |
| VII | H | Cl | OC$_3$H$_7$ | OC$_3$H$_7$ | 19 |
| VIII | H | Cl | CH$_3$ | C$_3$H$_7$ | liquid |
| IX | H | Cl | C$_3$H$_7$ | C$_3$H$_7$ | liquid |
| X | H | CH$_3$ | OCH$_3$ | OC$_2$H$_5$ | 38 |
| XI | H | CH$_3$ | OC$_2$H$_5$ | OC$_2$H$_5$ | 65 |
| XII | H | CH$_3$ | OC$_2$H$_5$ | OC$_3$H$_7$ | liquid |
| XIII | H | CH$_3$ | OC$_3$H$_7$ | OC$_3$H$_7$ | 17 |
| XIV | H | CH$_3$ | CH$_3$ | OC$_2$H$_5$ | liquid |
| XV | H | CH$_3$ | CH$_3$ | OC$_3$H$_7$ | liquid |
| XVI | H | CH$_3$ | CH$_3$ | OC$_4$H$_9$ | liquid |
| XVII | Cl | Cl | CH$_3$ | CH$_3$ | 73–7 |
| XVIII | Cl | Cl | OCH$_3$ | OCH$_3$ | 70 |
| XIX | Cl | Cl | OC$_2$H$_5$ | OC$_2$H$_5$ | 84–5 |
| XX | Cl | CH$_3$ | OCH$_3$ | OCH$_3$ | 95 |
| XXI | Cl | CH$_3$ | OC$_2$H$_5$ | OC$_2$H$_5$ | 94 | mice. DCP was less toxic than either DDT or methoxychlor with respect to fish, indicating that DCP is an environmentally safer insecticide for use in and around fish containing environments. In the biodegradability studies, DCP was found to be more biodegradable than methoxychlor.

Using techniques similar to those employed in Example I, the other novel compositions shown in Table II were prepared. Three general methods of synthesis were used for the compounds listed in Table II: (A) condensation of 2 moles of a substituted benzene with 1 mole of an aliphatic aldehyde in excess cold acid mixture (composition varied from 50% glacial acetic: 50% conc. H$_2$SO$_4$ to 100% conc. H$_2$SO$_4$) to form form the symmetrical 1,1-diphenylalkane; (B) condensation of 1 mole each of 2 different substituted benzenes with 1 mole of an aliphatic aldehyde in 5 volumes of the aforementioned acid mixture to form as the major product an asymmetrical 1,1-diphenylalkane; (C) condensation of p-substituted phenyl alkyl carbinol with a substituted benzene using 1 mole of anhydrous AlCl$_3$ in ethanol-free chloroform to yield an asymmetrical 1,1-diphenylalkane. All methods utilized a 0° C. ice bath. All methods required magnetic stirring bars or mechanical stirring apparatus, and all reactions were broken down by pouring them over ice; extraction was with diethylether or Skellysolve B. Silica gel-hexane column chromatography was often required to obtain the desired product with a purity of 98%. Ethanol was used for crystallization and recrystallizations of the solids. All melting points are uncorrected.

TABLE III

| | | Insect Toxicities | | | | | | | | |
|---|---|---|---|---|---|---|---|---|---|---|
| | Musca domestica | Culex fatigans | | Musca domestica | | | Anopheles albimanus | | Phormia regina |
| Example No. | LD$_{50}$ (ug/g) (NAIDM strain) | larvae-LC$_{50}$ (ppm) | adults-LC$_{50}$ (ug/cm$^2$) | NAIDM (w/PB) | R$_{sp}$ strain DDT-resistant LD$_{50}$ (ug/g) | w/PB | Larvae LC$_{50}$ (ppm) | adults LC$_{50}$ (ug/cm$^2$) | LD$_{50}$ (ug/g) |
| II | >500 | 0.22 | 9.7 | 24.5 | >500 | 140 | >1 | 6.9 | >250 |
| III | 39 | 0.08 | 10 | 10 | 95 | 14 | .09 | 1.1 | 6.75 |
| IV | 47 | 0.15 | >160 | 4.7 | 100 | 4.8 | .15 | 27 | 12 |
| V | 9.5 | 0.054 | 56 | 2 | 18 | 4.9 | .047 | 7.9 | 4.62 |
| VI | 15.5 | 0.05 | >160 | 3.2 | 25 | 5.5 | .075 | 14.5 | 62.5 |
| VII | 28 | 0.12 | >160 | 10 | 85 | 42 | .16 | >160 | 42.5 |
| VIII | 65 | 0.18 | 12 | 29 | 155 | 85 | .18 | 7.2 | 97.5 |
| IX | 55 | 0.145 | >160 | 45 | 120 | 90 | .068 | 17 | >250 |
| X | 65 | 0.13 | 16.5 | 12 | 110 | 17.5 | .17 | 6.3 | 28.5 |
| XI | 21.5 | 0.08 | 14.3 | 3.5 | 38 | 12.5 | .028 | 4.5 | 14.5 |
| XII | 21 | 0.39 | >160 | 6.5 | 42 | 22.5 | .056 | 35 | 60.0 |
| XIII | 100 | 0.30 | >160 | 21.5 | 185 | 185 | .25 | >160 | 200 |
| XIV | 70 | 0.052 | 5.0 | 18 | 150 | 31 | .275 | 5 | 35.0 |
| XV | 175 | 0.55 | >160 | 100 | 370 | 220 | .42 | 29 | 250 |
| XVI | >500 | >1 | >160 | 240 | >500 | >500 | .19 | >160 | >250 |
| XVII | 145 | 0.20 | 8.0 | 18 | 270 | 7.0 | .13 | 5 | 8 |
| XVIII | 65 | 0.061 | >160 | 8 | 155 | 9.5 | .18 | 1.63 | 13.5 |
| XIX | 17.5 | 0.094 | >160 | 7 | 90 | 23.5 | .041 | 49 | 24 |
| XX | >500 | >1 | >160 | 12 | >500 | 26 | >1 | 16 | 75 |
| XXI | 115 | >1 | >160 | 12 | 180 | 25.5 | >1 | >160 | >250 |

As the results in Table I indicate, DCP alone is not as toxic as DDT or methoxychlor to DDT resistant and susceptible strains of houseflies. However, DCP when employed with piperonyl butoxide (P.B.), a common synergist, is at least as toxic as methoxychlor and considerably more toxic than DDT. DCP was also found to be considerably less toxic than DDT and comparable to methoxychlor with respect to oral administrations to Some of the aldehydes used were synthesized because they were not available commercially; in some cases the diethylacetal of an aldehyde was prepared because of its greater stability under acidic reaction conditions. The following methods were used to prepare the aliphatic aldehydes:

a. α-chloropropionaldehyde was prepared by the method of Dick(1962), bubbling $Cl_2$ through propionaldehyde in 6N aqueous HCl solution at 10° to 15° C. and distilled three times onto molecular sieve drying agent at a final b.p. of 86° C. Confirmation of structure was obtained with infrared and nmr spectrometry.

b. α,α-dichloropropionaldehyde was also prepared by the method of Dick (1962) by bubbling $Cl_2$ through α-chloropropionaldehyde in 10 N aqueous HCl solution at 30°–32° C. The final b.p. was 86° C. The infrared and nmr spectrometry confirmed the dichloropropionaldehyde structure.

c. 2-chloroisobutyraldehyde was synthesized by chlorination of isobutyraldehyde, using sulfuryl chloride; the method of Stevens and Gillis (1957) was used. The product distilled at 85°–89° C. at 760mm. Structure was confirmed by nmr and infrared spectrometry.

The following carbinols were synthesized as precursors for use in synthesizing certain of the insecticides, in each case by condensation of the carbinol with a substituted benzene. Aluminum chloride was used as the condensing agent.

1. p-methylphenyl isopropyl carbinol was synthesized from the Grignard reagent isopropyl magnesium bromide and p-tolualdehyde in anhydrous diethylether. The product was purified by vacuum distillation, boiling at 121° C. at 2.5 mm. IR and nmr confirmed the structure. The compound was a semiviscous liquid.

2. p-methylphenyl-α-chloroethyl carbinol was synthesized using the Grignard was cooled and α-chloropropionaldehyde was added slowly in a solution of anhydrous diethylether. This carbinol distilled at 108°–110° C. at 0.6 mm to a crude form which was used for reactions. nmr and IR characterization confirmed the semi-viscous liquid to be the desired product.

The compositions shown in Table II were tested and found to have the insecticidal activities set forth in Table III.

The compound of Example XI was further evaluated, according to the same procedure shown in Table I, for biodegradability properties and found to have:
B.I. (fish) = 1.24, B.I. (snail) = 0.3, E.M. (fish) = 1920 and E.M. (snail) = 42,590.

The persistence of some of the compounds of the present invention was evaluated and compared with that of ethoxychlor. In these tests, the compounds were applied to the plywood surfaces of test huts and the mortalities of adult mosquitoes contained in the huts were measured to determine the number of weeks that 50% mortality continued to occur. The results are shown in Table IV.

TABLE IV

| Example No. | Anopheles albimanus, $P_{50}f$ | Culex fatigans, $P_{50}f$ |
|---|---|---|
| ethoxychlor | >44 | 8 |
| III | >6 | >8 |
| V | >80 | >70 |
| XI | >44 | 40 |
| XIV | 6 | 4 |
| XIX | >20 | 40 |

$f$ = number of weeks that at least 50% mortality occurred.

The compounds of Example III, V, XI, XII, XIV, XIX and XXI were tested for mouse toxicity and all (except Example XIX, $LD_{50} < 300$) were found to have $LD_{50}$ values of at least 1000 (μg./g.) which indicates that those compounds are at least five times safer to mice than is ethoxychlor, and yet exhibit insecticidal activities at least generally comparable to ethoxychlor.

It seems apparent that in the future the insecticides used in rice paddies, near lakes, reservoirs or rivers must necessarily be safe to fish, since some degree of pollution of these waters is inevitable as a result of insecticide applications. The toxicants with the most favorable fish safety ratio and least bioaccumulation should be chosen for use in these situations.

The compounds of Example III, V, XI, XIV and XXI were further tested and compared with ethoxychlor to determine fish toxicities over a period of time. In these tests, green sunfish (*Lepomis cyanellus*) were subject to an initial concentration dosage of 0.1 ppm and the number of days that 100 percent mortalities occurred was observed. The results are shown in Table V.

TABLE V

| | Green Sunfish Toxicity |
|---|---|
| Example | Number of days 100% mortality |
| ethoxychlor | 21 |
| III | 0 |
| V | 4 |
| XI | >35 |
| XIV | 0 |
| XXI | 0 |

The compositions of the present invention can be formulated into insecticidal formulations using techniques known in the art, for example, in formulating DDT insecticides. Thus, dusts, water dispersions, emulsions and/or solutions can be formulated provided the carrier or solvent is compatible and inert in the sense that it does not react or interfere with the insecticidal and biodegradable characteristics. In some such formulations the use of a synergist, e.g., piperonyl butoxide, may advantageously be employed.

While the present invention has been described by reference to illustrative examples various modifications will be apparent to those skilled in the art and any such modifications are intended to be within the spirit and scope of the invention as defined by the appended claims.

What is claimed is:

1. A biodegradable insecticide having the formula,

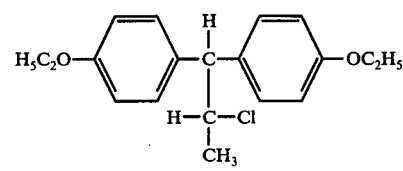

2. A biodegradable insecticide having the formula,

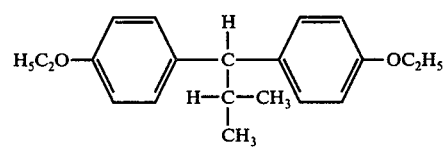

* * * * *